(12) United States Patent
Foody

(10) Patent No.: US 7,198,925 B2
(45) Date of Patent: Apr. 3, 2007

(54) PRE-TREATMENT OF BALES OF FEEDSTOCK

(75) Inventor: Brian Foody, Ottawa (CA)

(73) Assignee: Iogen Energy Corporation, Ottawa, Ontario (CA)

( * ) Notice: Subject to any disclaimer, the term of this patent is extended or adjusted under 35 U.S.C. 154(b) by 37 days.

(21) Appl. No.: 10/953,269

(22) Filed: Sep. 30, 2004

(65) Prior Publication Data

US 2006/0068475 A1 Mar. 30, 2006

(51) Int. Cl.
*C12P 19/02* (2006.01)
(52) U.S. Cl. ..................................... 435/105
(58) Field of Classification Search ............... 435/105
See application file for complete search history.

(56) References Cited

U.S. PATENT DOCUMENTS

| | | | |
|---|---|---|---|
| 3,357,437 A | 12/1967 | Maguire | 131/136 |
| 4,136,207 A | 1/1979 | Bender | 426/510 |
| 4,237,226 A | 12/1980 | Grethlein | 435/99 |
| 4,461,648 A | 7/1984 | Foody | 127/37 |
| 4,667,373 A | 5/1987 | Roder | 19/66 R |
| 5,366,558 A | 11/1994 | Brink | 127/43 |
| 5,424,417 A | 6/1995 | Torget et al. | 536/56 |
| 5,503,996 A * | 4/1996 | Torget et al. | 435/105 |
| 5,705,369 A * | 1/1998 | Torget et al. | 435/105 |
| 6,228,177 B1 * | 5/2001 | Torget | 127/37 |
| 6,557,267 B2 | 5/2003 | Wanger | 34/411 |
| 2002/0003032 A1 * | 1/2002 | Nay et al. | 162/21 |
| 2004/0231811 A1 * | 11/2004 | Engstrand et al. | 162/25 |

FOREIGN PATENT DOCUMENTS

GB 332052 9/1930

OTHER PUBLICATIONS

Grethlein, *Chemical Breakdown of Cellulosic Material*, J. Appl. Chem. Biotechnol, (1978), vol. 28, pp. 296-308.
Ghose, *Measurement of Cellulase Activities*, Pure and Appl. Chem., vol. 59, pp. 257-268, (1987).
Teleman et al., *Progress-curve Analysis Shows That Glucose Inhibits the Cellotriose Hydrolysis Catalysed by Celobiohydrolase II Trichoderma reesei*, Eur. J. Biochem., vol. 231, pp. 250-258, (1995).
International Search Report for PCT/CA2005/001494, mailed Jan. 3, 2006.

* cited by examiner

*Primary Examiner*—Herbert J. Lilling
(74) *Attorney, Agent, or Firm*—Cooley Godward Kronish LLP

(57) ABSTRACT

The present invention is directed to a method of pre-treating a lignocellulosic feedstock. The lignocellulosic feedstock comprises cereal straw, stover, or grass. One or more than one bale of lignocellulosic feedstock is conveyed into a pre-treatment reactor. Steam and acid are added to the bales and are maintained at a temperature, acid concentration, and for a time sufficient to hydrolyze hemicellulose to xylose and increase susceptibility of cellulose to digestion by cellulase enzymes, thus producing a pre-treated feedstock. The pre-treated feedstock is then removed from the pre-treatment reactor.

18 Claims, No Drawings

PRE-TREATMENT OF BALES OF FEEDSTOCK

The present invention relates to a method for the pre-treatment of feedstocks. More specifically, the present invention relates to a method for the pre-treatment of bales of feedstocks.

BACKGROUND OF THE INVENTION

Fuel ethanol is currently produced from feedstocks such as cornstarch, sugar cane, and sugar beets. However, the production of ethanol from these sources cannot expand much further due to limited farmland suitable for the production of such crops and competing interests with the human and animal food chain. Finally, the use of fossil fuels, with the associated release of carbon dioxide and other products, in the conversion process is a negative environmental impact of the use of these feedstocks.

The possibility of producing ethanol from cellulose-containing feedstocks such as agricultural wastes, grasses, and forestry wastes has received much attention due to the availability of large amounts of these inexpensive feedstocks, the desirability to avoid burning or landfilling cellulosic waste materials, and the cleanliness of ethanol as a fuel compared to gasoline. In addition, a byproduct of the cellulose conversion process, lignin, can be used as a fuel to power the cellulose conversion process, thereby avoiding the use of fossil fuels. Studies have shown that, taking the entire cycle into account, the use of ethanol produced from cellulose generates close to nil greenhouse gases.

The cellulosic feedstocks that may be used for ethanol production include (1) agricultural wastes such as corn stover, wheat straw, barley straw, canola straw, oat straw, and soybean stover; (2) grasses such as switch grass, miscanthus, cord grass, and reed canary grass, (3) forestry wastes such as aspen wood and sawdust, and (4) sugar processing residues such as bagasse and beet pulp.

Cellulose consists of a crystalline structure that is very resistant to breakdown, as is hemicellulose, the second most prevalent component. The conversion of cellulosic fibers to ethanol requires: 1) liberating cellulose and hemicellulose from lignin or increasing the accessibility of cellulose and hemicellulose within the cellulosic feedstock to cellulase enzymes, 2) depolymerizing hemicellulose and cellulose carbohydrate polymers to free sugars and, 3) fermenting the mixed hexose and pentose sugars to ethanol.

Among well-known methods used to convert cellulose to sugars is an acid hydrolysis process involving the use of steam and acid at a temperature, acid concentration and length of time sufficient to hydrolyze the cellulose to glucose (Grethlein, 1978, J. Appl. Chem. Biotechnol. 28:296–308). The glucose is then fermented to ethanol using yeast, and the ethanol is recovered and purified by distillation.

An alternative method of cellulose hydrolysis is an acid prehydrolysis (or pre-treatment) followed by enzymatic hydrolysis. In this sequence, the cellullosic material is first pre-treated using the acid hydrolysis process described above, but at milder temperatures, acid concentration and treatment time. This pre-treatment process is thought to increase the accessibility of cellulose within the cellulosic fibers for subsequent enzymatic conversion steps, but results in little conversion of the cellulose to glucose itself. In the next step, the pre-treated feedstock is adjusted to an appropriate temperature and pH, then submitted to enzymatic conversion by cellulase enzymes.

The hydrolysis of the cellulose, whether by acid or by cellulase enzymes, is followed by the fermentation of the sugar to ethanol, which is then recovered by distillation.

The temperatures typically used for acid hydrolysis or pre-treatment correspond to saturated steam pressures of 160 psig to 665 psig. The addition of sulphuric acid improves the digestion of the cellulose and shortens the time for pre-treatment from 5–30 minutes to 0.1–5 minutes. Achieving and maintaining these conditions requires a highly pressurized, acid-resistant system. U.S. Pat. No. 4,461,648 (Foody) describes equipment and conditions used in steam explosion pre-treatment, in which the feedstock, steam, and sulfuric acid are added to a reaction vessel, known as a steam gun. In the steam gun, steam is added and the steam pressure is increased rapidly to the desired pressure, followed by sudden explosive decompression. It produces a pre-treated material that is uniform, has most of the hemicellulose hydrolyzed to simple sugar, and requires less cellulase enzyme to hydrolyze the cellulose than other pre-treatment processes.

U.S. Pat. No. 4,461,648 (Foody) teaches that the feedstock materials are fed to the steam gun in a loose, divided form; that is, cut into small pieces and loosely packed. The use of wood chips from commercial chippers or straw cut into uniform pieces of 2–3 inches, as feedstocks is disclosed. Wood chips are loaded into the steam gun at a density of 13 pounds of solids (dry basis) in 1.2 cubic feet, or 10.83 pounds per cubic foot (174 kg/m$^3$). The solids loading of straw or grass in a steam gun is less, typically about 3 pounds per cubic foot.

The use of small, loosely packed pieces assists in penetrating the material uniformly with steam and dilute sulfuric acid. However, the use of such small, loosely packed pieces limits the amount of material that can be loaded into a given volume of steam gun. This increases the number or total volume of steam guns in a plant, which increases the overall cost of steam guns, which may reach the point of impracticality in process complexity and control. More importantly, cutting of the feedstock into small pieces requires power and chopping equipment, adding significantly to the cost of the process.

U.S. Pat. No. 4,136,207 (Bender) teaches steam pre-treatment of sawdust or wood chips measuring up to 4 inches, to produce a ruminant feed. The feedstock is saturated with moisture and compacted at 2000 psi to remove air and improve the subsequent penetration of steam. A rotating helical feed screw conveys the feedstock into a barrel, and steam is fed into the reactor barrel at 200–310 psi. The feedstock proceeds through the barrel, at the end of which is a valve to allow steam and volatiles to escape, and a product valve for treated solids to exit.

U.S. Pat. No. 5,366,558 (Brink) describes a continuous acid hydrolysis process of wood chips, ground forest waste, or other agricultural materials that occurs in several stages. The first stage is a steam treatment in the absence of acid. The material is then mechanically disintegrated to a very small particle size, acidified, and sensitized with oxygen. The sensitized material is then heated with steam for the final hydrolysis reaction. The material is washed countercurrently and the sugar stream and lignin are the products.

U.S. Pat. No. 4,237,226 (Grethlein) teaches a continuous pre-treatment system to enhance the enzymatic or acid hydrolysis of cellulose in oak wood chips. A 5% to 10% solids slurry is moved by a screw or positive displacement moving cavity pump. The slurry is heated to the reaction temperature and a concentrated stream of sulfuric acid is injected, resulting in a final acid concentration of 0 to 1% in the aqueous phase. The hot, acidified slurry is then held at the reaction temperature for the desired time of 1 minute or less. Rapid cooling quenches the reaction by flashing across an orifice or capillary at the outlet to the reactor. Grethlein uses wood chips that have been ground to pass through 60 mesh. In a similar process, U.S. Pat. No. 4,556,430 (Converse) includes a nonaqueous carrier in the feedstock system to decrease the amount of water present. Converse's system uses particulate matter, for example Wilner #247 wood chips or wood flour.

U.S. Pat. No. 5,424,417 (Torget) describes the pre-treatment of feedstock particles by flowing a hot acid or alkali stream through a bed of the particles. For ground wood, the preferred particle size is 0.1 mm to 30 mm. The particles are treated in the reactor at a solids concentration of 5% to 50%.

These pre-treatment processes use small, loosely packed materials, and suffer from the shortcomings associated with high power and equipment requirements for chopping, as well as a large volume requirement. Hence, high costs for pre-treatment.

U.S. Pat. No. 6,557,267 (Wanger) teaches a method of conditioning cotton with steam so as to improve fabric quality and reduce the presence of biological contaminants. A pressed cotton bale is placed in a closed container, from which air is evacuated to a reduced pressure of 50 to 200 mbar; steam is then introduced and permeates the bale for about 5 to 15 minutes, allowing the internal temperature of the bale to reach 60 to 80° C. The container is evacuated, and the procedure is repeated for a minimum of 4 cycles. However, treatment of this type has not been widely accepted in the treatment of lignocellulosic feedstock in ethanol production, as the temperatures are too low for an effective pretreatment.

SUMMARY OF THE INVENTION

The present invention relates to a method for the pre-treatment of feedstocks. More specifically, the present invention relates to a method for the pre-treatment of bales of feedstock.

It is an object of the present invention to provide a method for the pre-treatment of bales of feedstock.

The present invention provides a method (A) for conversion of a lignocellulosic feedstock to glucose comprising the steps of:
a. conveying one or more than one bale of the lignocellulosic feedstock into a pre-treatment reactor;
b. adding steam and acid to the bale, the steam and acid maintained at a temperature, acid concentration, and for a time sufficient to hydrolyze hemicellulose to xylose and increase susceptibility of cellulose to digestion by cellulase enzymes, to produce a pre-treated feedstock;
c. removing the pre-treated feedstock from the pre-treatment reactor;
d. depressurizing the pre-treatment reactor; and
e. hydrolysing the pre-treated feedstock using cellulase enzymes to produce glucose.

The present invention also provides a method (B) of pre-treating a lignocellulosic feedstock comprising the steps of:
a. conveying one or more than one bale of lignocellulosic feedstock into a pre-treatment reactor, the lignocellulosic feedstock comprising cereal straw, stover, or grass;
b. adding steam and acid to the bale, the steam and acid maintained at a temperature, acid concentration, and for a time sufficient to hydrolyze hemicellulose to xylose and increase susceptibility of cellulose to digestion by cellulase enzymes, to produce a pre-treated feedstock;
c. depressurizing the pre-treatment reactor; and
d. removing the pre-treated feedstock from the pre-treatment reactor.

The present invention also provides the method (A) or (B) defined above, wherein the feedstock is:
a cereal straw selected from the group consisting of wheat straw, barley straw, canola straw, and oat straw;
a stover selected from the group consisting of corn stover and soybean stover;
a grass selected from the group consisting of switch grass, miscanthus, cord grass, and reed canary grass; or any combination thereof.

The present invention pertains to the method (A) or (B) defined above, wherein the bale is soaked in water prior to the step of adding (step b). Alternatively, the bale may be cut prior to the step of conveying (step a). In another alternative, the feedstock may be pre-steamed after the step of conveying (step a) and prior to the step of adding (step b).

The present invention is also directed to the method (A) or (B) as described, wherein the acid added is sulfuric acid, sulfurous acid, sulfur dioxide, or a combination thereof.

The present invention also provides the method (A) or (B) defined above, wherein the temperature is about 160° C. to about 280° C., the acid concentration is about 0% to about 12% weight of acid on weight of feedstock, and the time is about 5 seconds to about 10 minutes.

Furthermore, in the method (A), after the step of removing (step d), the pre-treated feedstock may be subjected to enzymatic hydrolysis using cellulase enzymes.

The method of pre-treating the lignocellulosic feedstock as described above takes place in a much smaller volume than with loosely packed, divided feedstocks. This decreases the cost of the pre-treatment system, and hence the cost of making ethanol. A further savings is achieved by avoiding the need to cut to cut, chop, or grind the feedstock into small pieces. Furthermore, the need to handle and convey this material into the pre-treatment reactor is avoided. The direct use of bales circumvents the need for such additional processing.

DESCRIPTION OF PREFERRED EMBODIMENT

The present invention relates to a method for the pre-treatment of feedstocks. More specifically, the present invention relates to a method for the pre-treatment of bales of feedstock.

The following description is of a preferred embodiment by way of example only and without limitation to the combination of features necessary for carrying the invention into effect.

The present invention is directed to a batch method for direct pre-treatment of a bale of feedstock. One or more bales are conveyed into a pre-treatment reactor. The feedstock is then subjected to steam and acid for a time and temperature sufficient to hydrolyze hemicellulose and increase accessibility of the cellulose to digestion by cellulase enzymes. After the desired treatment conditions have been achieved, the system is rapidly decompressed and the reaction is terminated. The method increases the digestability of the cellulose in the feedstock by cellulase enzymes, which convert the cellulose to glucose.

According to an embodiment of the present invention, there is provided a method of pre-treating a lignocellulosic feedstock comprising the steps of:

a. conveying one or more than one bale of lignocellulosic feedstock into a pre-treatment reactor, the lignocellulosic feedstock comprising cereal straw, stover, or grass;
b. adding steam and acid to the bale, the steam and acid maintained at a temperature, acid concentration, and for a time sufficient to hydrolyze hemicellulose to xylose and increase susceptibility of cellulose to digestion by cellulase enzymes, to produce a pre-treated feedstock;
c. depressurizing the pre-treatment reactor; and
d. removing the pre-treated feedstock from the pre-treatment reactor.

The pre-treated feedstock may be further subjected to enzyme hydrolysis to produce a product of interest, for example but not limited to, glucose, as described herein.

By the term "lignocellulosic feedstock", "lignocellulosic material" or "lignocellulosic substrate" it is meant any type of biomass comprising cellulose such as, but not limited to non-woody plant biomass, agricultural wastes and forestry residues and sugar-processing residues. Generally, a lignocellulosic material is recognized as containing cellulose in an amount greater than about 25% (w/w), 15% hemicellulose, and 15% lignin. The cellulosic material can be of higher cellulose content, for example at least about 30% (w/w), 35% (w/w), 40% (w/w) or more.

In a non-limiting example, the lignocellulosic feedstock can include, but is not limited to grasses, such as switch grass, cord grass, rye grass, reed canary grass, miscanthus, or a combination thereof; sugar-processing residues such as, but not limited to sugar cane bagasse; agricultural wastes such as, but not limited to rice straw, rice hulls, barley straw, corn cobs, wheat straw, canola straw, oat straw, oat hulls, and corn fiber; stover, such as, but not limited to soybean stover, corn stover; and forestry wastes, such as, but not limited to recycled wood pulp fiber, sawdust, hardwood, softwood, or any combination thereof. Lignocellulosic feedstock may comprise one species of fiber, or alternatively lignocellulosic feedstock may comprise a mixture of fibers that originate from different lignocellulosic feedstocks. Agricultural wastes such as cereal straws, including wheat straw, barley straw, canola straw and oat straw; stovers such as corn stover and soybean stover; grasses such as switch grass, reed canary grass, cord grass, and miscanthus; or combinations thereof are particularly advantageous as lignocellulosic feedstocks.

The present invention is to be practiced with a lignocellulosic feedstock or a lignocellulosic material that has been baled. By the term "bale" or "baled feedstock", it is meant a feedstock as described above that has been bundled into the form of a bale, and in some instances bound using twine. Webster's Dictionary defines a bale as a large package of raw or finished material tightly bound with a twine or wire and often wrapped. The use of the term "bale" herein is consistent with this definition. The bales used in the present invention may be round or rectangular. The type of bale is not to be considered limiting, as variations on such bales is expected. Round bales are typically either about 4 feet in diameter and about 4 feet wide, or about 6 feet in diameter and about 5 feet wide. The smaller bales weigh about 390 to about 495 pounds, while the larger bales weigh about 1000 to about 1400 pounds. Rectangular bales are generally about 4 feet×about 4 feet×about 8 feet, and weigh about 1000–1250 pounds or about 4 feet×about 3 feet×about 7 feet and weigh about 660–825 pounds. Preferably, the material in the pre-treatment reactor is at least about 30 to about 60% solids, for example, 30, 35, 40, 45, 50, 55 or 60% solids. More preferably, the material in the pre-treatment reactor is about 50% solids. The typical density of a bale, whether round or rectangular, is 6.5 to 10.0 pounds of solids per cubic foot. As such, the solids packing in a steam gun is 1.5 to 3-fold higher with a bale than with the prior art loose-packing of small particles of straw, stover, or grass. For example, U.S. Pat. No. 4,416,648 (Foody) teaches the use of straw cut into uniform pieces of 2–3 inches that are loaded into the steam gun at a density of about 3 pounds per cubic foot.

The moisture content of either the round or rectangular bales may vary depending on the feedstock, storage conditions, and age of the bale. Generally, the moisture content of the bale may be about 5% to about 50%, or any amount therebetween. Preferably, the moisture content may be about 10% to about 20%, or any amount therebetween. For example, the moisture content may be about 5, 8, 10, 12, 15, 18, 20, 22, 25, 28, 30, 32, 35, 38, 40, 42, 45, 48, or 50%, or any amount therebetween.

Generally, bales are held together by twine, which may be synthetic, for example plastic or nylon, or natural, for example sisal. For the purposes of the present invention, either synthetic or natural twine may be used to bind the bales. The choice of synthetic or natural twine is familiar to those skilled in the art and may be a compromise between the resistance to degradation by mice when using synthetic twine, and avoiding removing the twine from the process when a natural twine is used.

In practicing the method of the present invention, the bound bale may be intact, or may be cut while maintaining the form of a bale. Those skilled in the art will recognize that, depending on the material and the nature of the bale, a bale may be cut 2 or more times and retain the general shape and integrity of a bale. Those skilled in the art will understand that the cutting of a bale might result in some distortion of shape, such as the slumping of round bales. The cut bales can then be pre-treated, without tying the bale back together. Without wishing to be bound by theory, cutting the bales may help promote better penetration of the acid and the high-pressure steam subsequently added to the feedstock.

The bale of lignocellulosic feedstock is conveyed into the pre-treatment reactor. The bale may be conveyed by any suitable method known in the art. For example, but without wishing to be limiting, the bale may be conveyed manually, by using a conveyor belt, by using a rail track, or any other method that is convenient. A single bale can be conveyed into a pre-treatment reactor, or more than one bale may be conveyed into the reactor, depending upon the size of the reactor. For example, which is not to be considered limiting in any manner, about 5 to 15 bales, or any amount therebetween may be conveyed and processed in the reactor; for example, about 5, 6, 7, 8, 9, 10, 11, 12, 13, 14, or 15 bales may be conveyed. In a non-limiting example, 11 bales may be conveyed into the pre-treatment reactor.

By the term "reactor" or "pre-treatment reacto", it is meant any vessel suitable for practising the method of the present invention. The dimensions of the pre-treatment reactor should be sufficient to accommodate the bale(s) conveyed into and out of the reactor, as well as additional headspace around the bale or bales. In a non-limiting example, the headspace extends about one foot around all the space occupied by the bales. Furthermore, the pre-treatment reactor should be constructed of a material capable of withstanding the pre-treatment conditions. Specifically, the construction of the reactor should be such that the pH, temperature and pressure do not affect the integrity of the vessel. For example, which is not to be considered limiting, the reactor may be run at temperatures corresponding to saturated steam pressures of 160 psig to 665 psig, and in the presence of an acid, for example, sulphuric acid (U.S. Pat. No. 4,461,648, which is incorporated herein by reference).

In a non-limiting example of the present invention, the bales may be soaked in water or other suitable liquid prior to the addition of steam or acid. The excess water is drained off the bales. The soaking of the bales in water may be done prior to conveying the bales into the reactor, or subsequent to the entry of the bales inside the pre-treatment reactor. Without wishing to be bound by theory, soaking the bales may help promote better penetration of the acid and the high-pressure steam subsequently added to the feedstock.

Once the bales are conveyed into the pre-treatment reactor, the reactor is sealed. A vacuum is pulled within the reactor to remove air from the bales for example a pressure of about 50 to about 300 mbar. Acid is added to the bales. The acid used in the method of the present invention may be any suitable acid known in the art; for example, but without wishing to be limiting in any manner, sulfuric acid, sulfurous acid, sulfur dioxide or a combination thereof may be used. The amount of acid added may be any amount sufficient to provide a good pre-treatment of the feedstock at the chosen pre-treatment temperature. For example, but without wishing to be limiting, the acid loading may be about 0% to about 12% by weight on the feedstock, or any amount therebetween; for example, the acid may be loaded at about 0, 1, 2, 3, 4, 5, 6, 7, 8, 9, 10, 11, or 12% by weight on the feedstock. In a non-limiting example, the acid is sulfur dioxide, and it is added to the bales by injecting the acid as a vapour to a concentration of 0.5% to 2.5% on weight of feedstock solids.

Steam is also added to the reactor at a saturated steam pressure of between about 100 psig to about 700 psig or any amount therebetween, for example 100, 150, 200, 250, 300, 350, 400, 450, 500, 550, 600, 650, or 700 psig, or any amount therebetween. More preferably, a saturated steam pressure from about 160 psig to about 665 psig is used. The acid and steam may be added in any order that is suitable to the present invention. For example, the acid may be added prior to, simultaneously with, or after the addition or injection of steam into the pre-treatment reactor.

The reactor is thus maintained at a temperature and pH for a length of time sufficient to hydrolyze a portion of the hemicellulose to xylose and to increase the digestibility of the cellulose by cellulase enzymes. The combination of time, temperature, and pH may be any suitable conditions known in the art. In a non-limiting example, the temperature, time and pH may be as described in U.S. Pat. No. 4,461,648, which is incorporated herein by reference.

The temperature may be of about 140° C. to about 280° C., or any temperature therebetween. More specifically, the temperature may be about 160° C. to about 280° C., or about 200° C. to about 260° C., or any temperature therebetween. For example, the temperature may be about 140, 150, 160, 170, 180, 190, 200, 210, 220, 230, 240, 250, 260, 270, or 280° C., or temperatures therebetween. Those skilled in the art will recognize that the temperature can vary within this range during the pre-treatment.

The pH in the pre-treatment reactor may be maintained at about 0.5 to about 2.5, or any pH therebetween; for example, the pH may be about 0.5, 0.8, 1.0, 1.2, 1.5, 1.8, 2.0, 2.2, or 2.5. In a non-limiting example, the pH in the pre-treatment reactor is about 0.5 to about 1.5, or about 0.8 to about 1.2. To achieve a pH within the specified range, generally about 0% to about 12% weight of acid on weight of solids must be added to the feedstock.

As will be understood by a person of skill in the art, the pre-treatment reaction time will depend on the temperature and acid concentration in the pre-treatment reactor. The pre-treatment time may be in the range of about 5 seconds and about 5 minutes, or any amount of time therebetween; for example, the pre-treatment time may be about 5 seconds, 30 seconds, 1, 1.5, 2, 2.5, 3, 3.5, 4, 4.5, or 5 minutes, or any amount therebetween. The pre-treatment time refers to the length of time the pre-treatment reactor is at a temperature between 160° C. and 280° C.

Once the desired pre-treatment reaction time has elapsed, the pre-treatment reaction may be terminated by opening the reactor, which releases the steam pressure and rapidly cools the reactor contents. The pre-treated material may then be removed from the reactor by any appropriate means known in the art, for example by conveying, exploding, dropping, washing, or slurrying. The pre-treated material may then be washed with water, or other suitable liquid to remove debris and twine from the bales.

In another example of the method according to the present invention, the feedstock bales may be pre-steamed. After conveying the bales to the reactor, and prior to the pre-treatment of the bales by steam and acid, the bales may be steamed at a steam pressure of about 30 to about 200 psig, or any pressure therebetween; for example, the steam pressure may be about 30, 40, 50, 60, 70, 80, 90, 100, 110, 120, 130, 140, 150, 160, 170, 180, 190, or 200 psig. The pre-steaming of the bales may be for a time of about 3 to about 30 minutes, or any time therebetween; for example, the time may be about 3, 5, 8, 10, 12, 15, 18, 20, 22, 25, 28, or 30 minutes. Without wishing to be bound by theory, the pre-steaming wets the solids and may help promote better penetration of the acid and the high-pressure steam subsequently added to the feedstock.

As familiar to those skilled in the art, enzymatic hydrolysis is carried out using cellulase enzymes, with the pH and temperature of the hydrolysis slurry chosen so as to be compatible with the enzyme, and hence could vary somewhat from the ranges stated below.

Following pre-treatment, the pre-treated material may be slurried in water or other suitable liquid at a solids concentration of about 4% to about 20%, or any concentration therebetween; for example, the solids concentration may be about 4, 5, 6, 7, 8, 9, 10, 11, 12, 13, 14, 15, 16, 17, 18, 19, or 20%. In a non-limiting example, the solids concentration is about 8% to about 15%.

The temperature of the slurry may then be adjusted to a temperature within the optimum range for the activity of cellulase enzymes. Generally, a temperature in the range of about 45° C. to about 55° C., or any temperature therebetween is suitable for most cellulase enzymes; for example, the temperature may be about 45, 46, 47, 48, 49, 50, 51, 52, 53, 54, or 55° C. However, the temperature of the slurry may be higher for thermophilic cellulase enzymes. The temperature of the slurry may be adjusted using any suitable method known in the art, for example, but not wishing to be limiting, by using cool water directly or a cooling jacket.

The pH of the slurry may also be adjusted to within the range of optimum pH for the cellulase enzymes used. Generally, the pH of the slurry is adjusted to a pH of about 4.5 to about 5.5, or any pH therebetween; for example, the pH may be about 4.5, 4.6, 4.7, 4.8, 4.9, 5.0, 5.1, 5.2, 5.3, 5.4, or 5.5. However, the pH of the slurry can be higher or lower than about 4.5 to 5.5 if the cellulase enzymes used are alkalophilic or acidophilic, respectively. It remains that the pH of the slurry should be adjusted to within the range of optimum pH for the enzymes used. The pH of the slurry may be adjusted using any suitable acid or base known in the art. For example, sodium hydroxide, ammonia, potassium hydrozide, ammonium hydroxide, ammonia, or other suitable base (if the slurry is acidic); or sulphuric acid, or other suitable acid (if the slurry is alkaline), may be used.

Cellulase enzymes are then added to the slurry. By the term "cellulase enzymes", "cellulase", or "enzymes", it is meant enzymes that catalyse the hydrolysis of cellulose to products such as glucose, cellobiose, and other cellooligosaccharides. Cellulase is a generic term denoting a multienzyme mixture comprising exo-cellobiohydrolases (CBH), endoglucanases (EG) and β-glucosidases (βG) that can be produced by a number of plants and microorganisms. The process of the present invention can be carried out with any type of cellulase enzymes, regardless of their source; however, microbial cellulases are generally available at lower cost than those of plants. Among the most widely studied, characterized, and commercially produced cellulases are those obtained from fungi of the genera *Aspergillus, Humicola*, and *Trichoderma*, and from the bacteria of the genera *Bacillus* and *Thermobifida*. Cellulase produced by the filamentous fungi *Trichoderma longibrachiatum* comprises at least two cellobiohydrolase enzymes termed CBHI and CBHII and at least three EG enzymes.

Cellulase enzymes work synergistically to degrade cellulose to glucose. CBHI and CBHII generally act on the ends of the glucose polymers in cellulose microfibrils liberating cellobiose (Teeri and Koivula, 1995, Carbohydr. Europe 12, 28–33) while the endoglucanases act at random locations on the cellulose. Together these enzymes hydrolyse cellulose to smaller cello-oligosaccharides such as cellobiose. Cellobiose is hydrolysed to glucose by β-glucosidase.

The cellulase enzyme dosage added to the slurry is chosen to achieve a sufficiently high level of cellulose conversion. For example, an appropriate cellulase dosage can be about 5.0 to about 50.0 Filter Paper Units (FPU or IU) per gram of cellulose, or any amount therebetween. For example, the cellulase dosage may be about 5, 8, 10, 12, 15, 18, 20, 22, 25, 28, 30, 32, 35, 38, 40, 42, 45, 48, or 50 FPU, or any amount therebetween. The FPU is a standard measurement familiar to those skilled in the art and is defined and measured according to Ghose (1987, Pure and Appl. Chem. 59:257–268). An adequate quantity of β-glucosidase (cellobiase) activity is also added to the mixture. The dosage level of β-glucosidase may be about 5 to about 400 β-glucosidase units per gram of cellulose, or any amount therebetween, or from about 35 to about 100 β-glucosidase units per gram of cellulose; for example, the dosage may be 35, 40, 45, 50, 55, 60, 65, 70, 75, 80, 85, 90, 95, 100, 125, 150, 175, 200, 225, 250, 275, 300, 325, 350, 375, or 400 β-glucosidase units per gram of cellulose, or any amount therebetween. The β-glucosidase unit is measured according to the method of Ghose (1987, Pure and Appl. Chem. 59:257–268).

The enzymatic hydrolysis continues for about 24 to about 250 hours, or any amount of time therebetween, depending on the degree of conversion desired. For example, the reaction time could be about 24, 30, 40, 50, 60, 70, 80, 90, 100, 110, 120, 130, 140, or 150 hours, or any amount therebetween. The resulting slurry is an aqueous solution of glucose and xylose with lignin and other unconverted, suspended solids. The sugars are readily separated from the suspended solids and fermented to ethanol by yeast.

The above description is not intended to limit the claimed invention in any manner, Furthermore, the discussed combination of features might not be absolutely necessary for the inventive solution.

The present invention will be further illustrated in the following examples. However, it is to be understood that these examples are for illustrative purposed only, and should not be used to limit the scope of the present invention in any manner.

The invention claimed is:

1. A method for conversion of a lignocellulosic feedstock to glucose comprising the steps of:
   a. conveying one or more than one bale of the lignocellulosic feedstock into a pre-treatment reactor;
   b. adding steam and acid to the bale, the steam and acid maintained at a temperature, acid concentration, and for a time sufficient to hydrolyze hemicellulose to xylose and increase susceptibility of cellulose to digestion by cellulase enzymes, to produce a pre-treated feedstock;
   c. depressurizing the pre-treatment reactor;
   d. removing the pre-treated feedstock from the pre-treatment reactor; and
   e. hydrolysing the pre-treated feedstock using cellulase enzymes to produce glucose.

2. The method of claim 1, wherein the lignocellulosic feedstock is a cereal straw, stover, a grass, or any combination thereof.

3. The method of claim 2, wherein the cereal straw is a wheat straw, barley straw, canola straw, or oat straw; the stover is corn stover or soybean stover; and the grass is switch grass, miscanthus, cord grass, or reed canary grass.

4. The method of claim 1, wherein the bale is soaked in water prior to the step of adding (step b).

5. The method of claim 1, wherein the bale is cut prior to the step of conveying (step a).

6. The method of claim 1, wherein after the step of conveying (step a) and prior to the step of adding (step b), the feedstock is pre-steamed.

7. The method of claim 1, wherein in the step of adding (step b), the acid is selected from the group consisting of sulfuric acid, sulfurous acid, sulfur dioxide, and a combination thereof.

8. The method of claim 1, wherein in the step of adding (step b), the temperature is about 160° C. to about 280° C., the acid concentration is about 0% to about 12% weight of acid on weight of feedstock, and the time is about 5 seconds to about 10 minutes.

9. The method of claim 1 wherein in the step of conveying (step a) the lignocellulosic feedstock in the pre-treatment reactor is at least 50% solids.

10. A method for pre-treating a lignocellulosic feedstock comprising the steps of:
   a. conveying one or more than one bale of lignocellulosic feedstock into a pre-treatment reactor, the lignocellulosic feedstock comprising cereal straw, stover, or grass;
   b. adding steam and acid to the bale, the steam and acid maintained at a temperature, acid concentration, and for a time sufficient to hydrolyze hemicellulose to xylose and increase susceptibility of cellulose to digestion by cellulase enzymes, to produce a pre-treated feedstock;
   c. depressurizing the pre-treatment reactor; and
   d. removing the pre-treated feedstock from the pre-treatment reactor.

11. The method of claim 10, wherein the lignocellulosic feedstock is a cereal straw, stover, a grass, or any combination thereof.

12. The method of claim 11, wherein the cereal straw is a wheat straw, barley straw, canola straw, or oat straw; the stover is corn stover or soybean stover; and the grass is switch grass, miscanthus, cord grass, or reed canary grass.

13. The method of claim 10, wherein the bale is soaked in water prior to the step of adding (step b).

14. The method of claim 10, wherein the bale is cut prior to the step of conveying (step a).

15. The method of claim 10, wherein after the step of conveying (step a) and prior to the step of adding (step b), the feedstock is pre-steamed.

16. The method of claim 10, wherein in the step of adding (step b), the acid is selected from the group consisting of sulfuric acid, sulfurous acid, sulfur dioxide, and a combination thereof.

17. The method of claim 10, wherein in the step of adding (step b), the temperature is about 160° C. to about 280° C., the acid concentration is about 0% to about 12% weight of acid on weight of feedstock, and the time is about 5 seconds to about 10 minutes.

18. The method of claim 10, wherein in the step of conveying (step a) the lignocellulosic feedstock in the pre-treatment reactor is at least 50% solids.

* * * * *